United States Patent

Prasad

[11] Patent Number: 6,103,383
[45] Date of Patent: Aug. 15, 2000

[54] HIGH TUNGSTEN, SILICON-ALUMINUM DENTAL ALLOY

[75] Inventor: Arun Prasad, Cheshire, Conn.

[73] Assignee: Jeneric/Pentron Incorporated, Wallingford, Conn.

[21] Appl. No.: 09/013,950

[22] Filed: Jan. 27, 1998

[51] Int. Cl.⁷ ..................................... B32B 17/00
[52] U.S. Cl. .................. 428/428; 428/457; 428/469; 428/472; 420/428; 420/442; 420/443; 420/445; 433/200.1; 433/207
[58] Field of Search ..................... 420/428, 442, 420/445, 443; 106/35; 428/457, 469, 472, 428, 432; 433/207, 200.1

[56] References Cited

U.S. PATENT DOCUMENTS

| | | |
|---|---|---|
| 3,304,177 | 2/1967 | Wlodek . |
| 3,617,261 | 11/1971 | Lherbier et al. . |
| 3,841,868 | 10/1974 | Dudek et al. . |
| 3,896,547 | 7/1975 | Kulwiec . |
| 3,914,867 | 10/1975 | Manning et al. . |
| 3,948,653 | 4/1976 | Tesk et al. . |
| 4,053,308 | 10/1977 | Tesk et al. . |
| 4,080,201 | 3/1978 | Hodge et al. . |
| 4,114,272 | 9/1978 | Saragossi . |
| 4,210,447 | 7/1980 | Tsai . |
| 4,243,412 | 1/1981 | Tandon . |
| 4,249,943 | 2/1981 | Mohammed et al. . |
| 4,392,829 | 7/1983 | Tanaka . |
| 4,556,534 | 12/1985 | Burnett .................................. 420/455 |
| 4,812,288 | 3/1989 | Tamba .................................. 420/433 |

FOREIGN PATENT DOCUMENTS

| | | |
|---|---|---|
| 0 381 121 | 8/1990 | European Pat. Off. . |
| 25 28 547 | 7/1976 | Germany . |
| 27 13 755 | 10/1978 | Germany . |
| 35 40 323 | 5/1987 | Germany . |
| 41 10 543 | 10/1992 | Germany . |
| 2 038 359 | 7/1980 | United Kingdom . |

*Primary Examiner*—Timothy M. Speer
*Attorney, Agent, or Firm*—Cantor Colbun LLP

[57] ABSTRACT

A new nickel-chromium alloy having high rigidity, castability, corrosion and oxidation resistance and easy workability is disclosed. The alloy comprises from about 45 to 81% nickel by weight, from about 13 to 25% chromium by weight, from about 3 to 15% tungsten by weight, and silicon and aluminum in the range from about 1 to about 6% by weight each. The new alloy has a high concentration of tungsten.

6 Claims, No Drawings

HIGH TUNGSTEN, SILICON-ALUMINUM DENTAL ALLOY

BACKGROUND OF THE INVENTION

1. Field of the Invention

This invention relates to materials for dental prosthetic devices such as tooth fillings. In particular, this invention relates to a beryllium-free nickel-chromium-tungsten alloy further comprising silicon and aluminum. The alloy of this invention bonds well to porcelains commonly used in dental restorations.

2. Brief Description of the Prior Art

Fixed and removable dental prostheses such as crowns, artificial teeth, and bridges have traditionally been made using alloys of precious metals such as gold or palladium. Such alloys bond well with porcelains and resin-base composites. However, given the increasing expense of precious metals, substitute materials have been sought for years.

Over the last fifteen years, nickel-chromium alloys containing less than two percent beryllium by weight have emerged as successful alternatives based on the alloys' unique mechanical and thermal properties. Such nickel-chromium alloys have a higher modulus of elasticity than precious metal alloys, are light in weight, and have a low thermal conductivity. These alloys currently occupy a high percentage of the dental restoration market. However, because of concerns over the allergenic and toxicity potentials of beryllium, some consider such alloys to be health hazards, and the use of beryllium is becoming disfavored. Certain countries have gone so far as to pass regulations banning the use of beryllium in dental alloy materials. Beryllium-containing alloys also exhibit inferior corrosion resistance in acidic environments (lower pHs) compared to alloys that do not contain beryllium.

A number of patents describe beryllium-free nickel-chromium alloys, for example U.S. Pat. No. 3,914,867 to Manning et al.; U.S. Pat. No. 3,896,547 to Kulwiec; U.S. Pat. No. 3,841,868 to Dudek et al; U.S. Pat. No. 3,948,653 to Tesk et al.; U.S. Pat. No. 4,053,308 to Tesk et al.; U.S. Pat. No. 4,114,272 to Saragossi; U.S. Pat. No. 4,210,447 to Tsci and U.S. Pat. No. 4,243,412 to Tandon, as well as German Patent No. 2713755 to Rademacher. Many of the nickel-chromium alloys based on the above patents were introduced in the market and used by the dental profession with varying degrees of success. However, none of these alloys have successfully replaced beryllium-containing alloys.

In fact, the majority of these beryllium-free alloys have been withdrawn from the market because of their limited success. Such products have likely failed due to their poor castability, and the green color of the oxides formed on the alloys' surfaces. It is also likely difficult to control the amount of oxide formation, thereby resulting in poor adhesion and inferior mechanical properties. Accordingly, there remains a need for a dental alloy with the advantageous properties of beryllium-containing nickel-chromium alloys, but that will avoid the health hazard concerns associated with these alloys.

SUMMARY OF THE INVENTION

The above-described drawbacks and deficiencies of the prior art are alleviated by the beryllium-free nickel-chromium alloy of the present invention, wherein the alloy comprises from about 45 to 81% nickel by weight, from about 13 to 25% chromium by weight, from about 3 to 15% tungsten by weight, and silicon and aluminum in the range from about 1 to about 6% by weight each. The new alloy thus has a high concentration of tungsten. The alloy has high rigidity, good castability, corrosion and oxidation resistance and easy workability. Such alloy is suitable for preparation of dental prosthesis and has a comparable performance compared to popular commercial beryllium-containing nickel-chromium alloys.

DETAILED DESCRIPTION OF THE INVENTION

The relative proportions of the various elements comprising the alloy compositions in accordance with the present invention enable the alloy to retain the advantageous properties associated with nickel-chromium alloys, while at the same time eliminating the presence of beryllium completely.

In an important feature of the present invention, the alloy is beryllium-free. "Beryllium-free" as used herein is intended to mean an alloy which has no added beryllium, notwithstanding any trace impurities present in the other components of the alloy. In particular, the compositions (approximate percent by weight) of the alloys of the invention are set forth in the following Table 1:

TABLE 1

| COMPONENT | BROAD RANGE | PREFERRED RANGE |
| --- | --- | --- |
| Nickel | 45–82% | 58–71% |
| Chromium | 13–25% | 18–22% |
| Tungsten | 3–15% | 8–12% |
| Silicon | 1–6% | 2–4% |
| Aluminum | 1–6% | 2–4% |
| Rare earth metals | 0–2% | 0–0.5% |
| Carbon | 0–0.5% | 0–.1% |

The alloys of this invention must contain the essential ingredients enumerated above. However, other components may also be included within the composition, excepting, of course, beryllium. A number of substitutions known to those of skill in the art may further be made for a portion of the above compositions. For example, a part of the nickel component may be replaced by iron, copper, cobalt, gold, platinum, or silver. A portion of the tungsten and chromium components may be replaced by molybdenum, tantalum, vanadium, or niobium. A portion of the silicon and aluminum components may be replaced by boron, zirconium, titanium, indium, tin, gallium, germanium, manganese, hafnium and zinc.

The alloys of this invention are suitable to be shaped by any of the techniques usually employed in forming prosthetic devices for alloys. Particularly for dental prosthetic devices, the initial step in shaping an alloy requires melting in air, followed by casting. The resulting cast article is subjected to a heat-treatment to develop a thin oxide which adheres tightly to the metal, and is compatible with the dental porcelains that are generally employed for coating such devices. Dental porcelain may be applied in one or more layers, as is conventional in the art. For example, the metal shaped as a prosthetic device may first be coated with an opaque layer to mask the metal, after which it is coated with a dentine layer, and finally coated with a vitreous enamel layer to produce a natural, translucent, tooth-like appearance.

The following examples demonstrate the advantages of the alloy of the instant invention.

A number of alloys in accordance with the present invention were prepared and compared to prior art beryllium-containing and beryllium-free alloys, including Rexillium III, available from Jeneric®/Pentron®, Inc., Wallingford, Conn. Rexillium III is a popular commercial beryllium-containing nickel-chromium alloy.

The compositions of the tested alloys are shown in Table 2 on the basis of weight percentage. Sample alloy BC1 has the approximate composition of the control alloy Rexillium III. The compositions of samples BF1, BF2, BF3, and BF4 are based on U.S. Pat. Nos. 4,210,447, 3,948,653, 4,243,412, and German Patent No. 2713755 respectively. The compositions of sample alloys BF5–BF15 exemplify the alloys in accordance with the present invention. A review of earlier patents and literature indicates that molybdenum has been used as a key component in the development of beryllium-free nickel-chromium alloys. In accordance with the present invention, emphasis is placed primarily on the use of tungsten in conjunction with an appropriate amount of silicon and aluminum.

Sample alloy BF5 is a high silicon and aluminum composition. Sample alloy BF6 shows the effect of substituting tungsten for niobium.

Sample alloys BF7 through BF9 reflect influences resulting from a variation in the amount of tungsten and molybdenum while maintaining their sum to a constant value of 8.50%.

Sample alloys BF10 through BF12 show effects resulting from the changes in titanium concentration.

The alloys BF13 and BF14 show the effect of an increase in the total amount of silicon and aluminum. These two alloys are not only molybdenum-free, but also contain much higher amounts of tungsten. The effect of the addition of lanthanum is shown by comparison of sample BF15 with sample BF14.

It has been found to be preferable that a lower quantity of silicon be used together with higher quantities of aluminum and conversely, that lower a lower quantity of aluminum be used together with a higher quantity of silica. Higher concentrations of silicon or aluminum beyond 6% tend to embrittle the alloys.

Castability is determined by making three castings of a pattern (designed from a plastic mesh) from each alloy utilizing the lost wax technique. The temperatures of the mold are maintained constant at 1500° F. Melting is performed using a gas-oxygen torch. After retrieving the cast pattern from the mold, the number of squares filled or cast are counted. Percentage of filled squares is calculated using the average number of filled squares divided by the total number of squares.

The reaction of the alloy with the mold and crucible is based on the following factors: (a) difficulty in removing the investment from the casting; (b) difficulty in removing the slag left over in the crucible; and discoloration of the surface of the crucible.

Oxide color is determined by casting three small flag patterns from each alloy. After divesting, the surface of each flag is ground and blasted with 50 um of aluminum oxide abrasives, cleaned ultrasonically for five minutes, and dried with a facial tissue paper. These pieces are then subjected to degassing treatment from 1200 to 1825° F. under vacuum. Following that procedure they are bench cooled and the color of the oxide noted.

Coefficient of thermal expansion is determined in a Theta Differential Dilatometer using a 3 mm×50 mm sample. Each sample underwent a thermal treatment from 650° C. to 950° C. with ten minute hold at 950° C. The measurement of thermal expansion was carried using pure gold as the standard. The heating rate used was 10° C./minute, with a temperature range of 25–700° C. The average coefficient of thermal expansion between 25–500° C. was calculated from the plots.

Porcelain adherence is measured using the following procedure:

a) Casting 3 copings from each alloy;
b) Metal preparation and degassing at 1825° F. under vacuum;
c) Building a commercially-available porcelain, such at the porcelain distributed by Vita Zahnfabrik under the tradename VMK68 Porcelain;

TABLE 2

| Component | BC1 | BF1 | BF2 | BF3 | BF4 | BF5 | BF6 | BF7 | BF8 | BF9 | BF10 | BF11 | BF12 | BF13 | BF14 | BF15 | BF16 |
|---|---|---|---|---|---|---|---|---|---|---|---|---|---|---|---|---|---|
| Ni | 75.20 | 61.90 | 65.40 | 66.00 | 69.00 | 61.50 | 61.25 | 69.50 | 69.50 | 69.50 | 62.50 | 61.75 | 60.75 | 63.00 | 62.00 | 61.75 | 59.75 |
| Cr | 14.00 | 22.00 | 13.50 | 17.00 | 20.50 | 22.00 | 22.00 | 18.00 | 18.00 | 18.00 | 25.00 | 25.00 | 25.00 | 22.00 | 22.00 | 22.00 | 22.00 |
| W | — | — | — | — | — | — | 4.50 | 3.00 | 4.25 | 6.00 | 3.00 | 3.00 | 3.00 | 11.00 | 11.00 | 11.00 | 11.00 |
| Mo | 6.00 | 8.50 | 7.25 | 5.00 | 6.00 | 8.50 | 8.25 | 5.50 | 4.25 | 2.50 | 5.50 | 5.50 | 5.50 | — | — | — | — |
| Nb | — | 4.00 | — | 5.00 | — | 4.00 | — | — | — | — | — | — | — | — | — | — | — |
| Fe | — | 2.00 | 5.00 | 5.00 | — | — | — | — | — | — | — | — | — | — | — | — | — |
| Si | — | 0.50 | 1.00 | 1.00 | 3.50 | 2.50 | 2.50 | 2.50 | 2.50 | 2.50 | 2.50 | 2.50 | 2.50 | 2.00 | 3.00 | 3.00 | 3.00 |
| Al | 2.50 | 0.10 | 0.50 | 1.00 | — | 1.00 | 1.00 | 1.00 | 1.00 | 1.00 | 1.00 | 1.00 | 1.00 | 2.00 | 2.00 | 2.00 | 4.00 |
| Ti | 0.25 | 0.20 | — | — | — | 0.25 | 0.25 | 0.25 | 0.25 | 0.25 | 0.25 | 1.00 | 2.00 | — | — | — | — |
| La/Ce | — | 0.50 | — | — | 0.50 | 0.25 | 0.25 | 0.25 | 0.25 | 0.25 | 0.25 | 0.25 | 0.25 | — | — | 0.25 | 0.25 |
| Be | 1.80 | — | — | — | — | — | — | — | — | — | — | — | — | — | — | — | — |
| Co | 0.25 | — | — | — | — | — | — | — | — | — | — | — | — | — | — | — | — |
| Mn | — | 0.30 | 0.10 | — | — | — | — | — | — | — | — | — | — | — | — | — | — |
| B | — | — | — | — | 0.50 | — | — | — | — | — | — | — | — | — | — | — | — |
| Ga | — | — | 7.25 | — | — | — | — | — | — | — | — | — | — | — | — | — | — |

The alloys were tested for castability, reaction with mold and crucible materials, oxide color after degassing, coefficient of thermal expansion, porcelain adherence, mechanical properties and melting range. Table 3 lists the parameters studied for the above alloys. The tests used in the evaluation of these parameters are as follows.

d) Cutting a groove using diamond disc at the incisal edge up to the opaque layer and applying a shear force on two sides using a screw driver;
e) Evaluating the bond based on amount of porcelain debonding, assigning a rating of "excellent" where more than 75% stayed stuck, "good" where between 50–75% stayed stuck, and "poor" where less than 50% stayed stuck.

Mechanical properties are evaluated using three tensile specimens cast from each alloy. The specimens are subjected to a heat treatment from 650° C. to 950° C. with 10 minute hold at the upper temperature. They are then tested for yield strength, ultimate tensile strength, and elongation using an Instron machine with the cross-head speed set at 0.5 inches per minute.

The melting range (solidus and liquidus) of the sample alloys are obtained using a differential thermal analyzer.

TABLE 3

| Parameters Studied | Sample Number | | | | | | | |
|---|---|---|---|---|---|---|---|---|
| | BC1 | BF1 | BF2 | BF3 | BF4 | BF5 | BF6 | BF7 |
| Castability (% Filled) | 98 | 80 | 90 | 85 | 96 | 90 | 88 | 86 |
| Reaction with mold, crucible | no | yes | yes | yes (less) | yes | no | no | no |
| Oxide Color | straw | greenish-grey | greenish-grey | grey | greenish-grey | dark grey | blue-grey | blue-grey |
| Coeff. of Thermal Exp. (ppm) | 14 | 13.8 | 148 | 14.2 | 14.3 | 13.5 | 13.66 | 14.25 |
| Porcelain Adherence | excellent | good | good | good | good | good | good | good |
| Yield Strength (Mpa) | 793 | 345 | 265 | 380 | 440 | 436 | 379 | — |
| U.T.S. (Mpa) | 1130 | 520 | 450 | 655 | — | 460 | 487 | — |
| Elongation (%) | 13 | 18 | 10 | 5.5 | 4 | 0.5 | 2.5 | — |

| Parameters Studied | Sample Number | | | | | | | | |
|---|---|---|---|---|---|---|---|---|---|
| | BF8 | BF9 | BF10 | BF11 | BF12 | BF13 | BF14 | BF15 | BF16 |
| Castability (% Filled) | 85 | 86 | 88 | 86 | 80 | 90 | 95 | 95 | 92 |
| Reaction with mold, crucible | no | no | no | no | no | no | no | no | no |
| Oxide Color | blue-grey | blue-grey | blue-grey | blue-grey | blue-grey | blue-grey | light grey | med grey | med grey |
| Coeff. of Thermal Exp. (ppm) | 14.2 | 14.3 | 13.81 | 14.2 | 13.57 | 14.07 | 14.1 | 14.1 | 14.3 |
| Porcelain Adherence | good | excellent | good | good | good | excellent | excellent | excellent | good |
| Yield Strength (Mpa) | — | — | — | 336 | 386 | 524 | 483 | 485 | |
| U.T.S. (Mpa) | — | — | — | 406 | 548 | 581 | 628 | 650 | |
| Elongation (%) | — | — | — | 3 | 8.5 | 1.5 | 12 | 14 | |

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A chromium-nickel alloy comprising
   nickel in an amount from about 45 to 81 percent by weight;
   chromium in an amount from about 13 to 25 percent by weight;
   tungsten in an amount from about 8 to 15 percent by weight;
   silicon in an amount from about 1 to 6 percent by weight;
   aluminum in an amount from about 1 to 6 percent by weight;
   rare earth metals in an amount up to about 2 percent by weight;
   carbon in an amount up to about 0.5 % by weight; wherein the alloy is beryllium-free.

2. The chromium-nickel of claim 1, wherein the alloy comprises
   nickel in an amount from about 58 to 71 percent by weight;
   chromium in an amount from about 18 to 22 percent by weight;
   tungsten in an amount from about 8 to 15 percent by weight;
   silicon in an amount from about 1 to 6 percent by weight;
   aluminum in an amount from about 1 to 6 percent by weight;
   rare earth metals in an amount up to about 2 percent by weight;
   carbon in an amount up to about 0.5 % by weight; wherein the alloy is beryllium-free.

3. A dental restoration comprising
   a dental alloy coated with a dental composite, wherein the dental alloy comprises
   nickel in an amount from about 45 to 81 percent by weight;
   chromium in an amount from about 13 to 25 percent by weight;
   tungsten in an amount from about 8 to 15 percent by weight;
   silicon in an amount from about 1 to 6 percent by weight;
   aluminum in an amount from about 1 to 6 percent by weight;

rare earth metals in an amount up to about 2 percent by weight;

carbon in an amount up to about 0.5 % by weight; wherein the alloy is beryllium-free.

4. The dental restoration of claim 3, wherein the dental alloy comprises nickel in an amount from about 58 to 71 percent by weight;

chromium in an amount from about 18 to 22 percent by weight;

tungsten in an amount from about 8 to 15 percent by weight;

silicon in an amount from about 1 to 6 percent by weight;

aluminum in an amount from about 1 to 6 percent by weight;

rare earth metals in an amount up to about 2 percent by weight;

carbon in an amount up to about 0.5 % by weight; wherein the alloy comprises no beryllium.

5. A dental restoration, comprising a porcelain jacket fired on a body of a dental alloy, the dental alloy comprising nickel in an amount from about 45 to 81 percent by weight;

chromium in an amount from about 13 to 25 percent by weight;

tungsten in an amount from about 8 to 15 percent by weight;

silicon in an amount from about 1 to 6 percent by weight;

aluminum in an amount from about 1 to 6 percent by weight;

rare earth metals in an amount up to about 2 percent by weight;

carbon in an amount up to about 0.5 % by weight; wherein the alloy is beryllium-free.

6. The dental restoration of claim 5, wherein the alloy comprises nickel in an amount from about 58 to 71 percent by weight;

chromium in an amount from about 18 to 22 percent by weight;

tungsten in an amount from about 8 to 15 percent by weight;

silicon in an amount from about 1 to 6 percent by weight;

aluminum in an amount from about 1 to 6 percent by weight;

rare earth metals in an amount up to about 2 percent by weight;

carbon in an amount up to about 0.5 % by weight; wherein the alloy is beryllium-free.

* * * * *

UNITED STATES PATENT AND TRADEMARK OFFICE
CERTIFICATE OF CORRECTION

PATENT NO. : 6,103,383
DATED : August 15, 2000
INVENTOR(S) : Arun Prasad

It is certified that error appears in the above-identified patent and that said Letters Patent is hereby corrected as shown below:

Column 5,
Table 3, under column 4 labeled "BF2" delete "148" and insert therefor -- 14.8 --

Signed and Sealed this

Sixteenth Day of December, 2003

JAMES E. ROGAN
*Director of the United States Patent and Trademark Office*